United States Patent [19]

Tomonto et al.

[11] Patent Number: 5,733,326
[45] Date of Patent: Mar. 31, 1998

[54] COMPOSITE MATERIAL ENDOPROSTHESIS

[75] Inventors: Charles V. Tomonto, Miami; Robert J. Cottone, Jr., Ft. Lauderdale; John L. Barchi, Hollywood, all of Fla.

[73] Assignee: Cordis Corporation, Miami Lakes, Fla.

[21] Appl. No.: 654,165

[22] Filed: May 28, 1996

[51] Int. Cl.⁶ ........................................................ A61F 2/06
[52] U.S. Cl. ..................................... 623/1; 623/12
[58] Field of Search ......................... 623/1, 11, 12; 606/194, 195, 198

[56] References Cited

U.S. PATENT DOCUMENTS

| | | |
|---|---|---|
| 3,278,176 | 10/1966 | Abolins . |
| 3,842,441 | 10/1974 | Kaiser . |
| 3,868,956 | 3/1975 | Alfidi et al. . |
| 4,023,557 | 5/1977 | Thorne et al. . |
| 4,214,587 | 7/1980 | Sakura, Jr. . |
| 4,501,264 | 2/1985 | Rockey . |
| 4,641,653 | 2/1987 | Rockey . |
| 4,733,665 | 3/1988 | Palmaz . |
| 4,763,653 | 8/1988 | Rockey . |
| 4,768,507 | 9/1988 | Fischell et al. . |
| 4,776,337 | 10/1988 | Palmaz . |
| 4,795,458 | 1/1989 | Regan . |
| 4,800,882 | 1/1989 | Gianturco . |
| 4,813,925 | 3/1989 | Anderson, Jr. et al. . |
| 4,830,003 | 5/1989 | Wolff et al. . |
| 4,848,343 | 7/1989 | Wallsten et al. . |
| 4,856,516 | 8/1989 | Hillstead . |
| 4,878,906 | 11/1989 | Lindenmann et al. . |
| 4,994,033 | 2/1991 | Shockey et al. . |
| 5,001,825 | 3/1991 | Halpern . |
| 5,019,090 | 5/1991 | Pinchuk . |
| 5,064,435 | 11/1991 | Porter . |
| 5,071,407 | 12/1991 | Termin et al. . |
| 5,102,417 | 4/1992 | Palmaz . |
| 5,133,732 | 7/1992 | Wiktor . |
| 5,135,536 | 8/1992 | Hillstead . |
| 5,195,984 | 3/1993 | Schatz . |
| 5,201,757 | 4/1993 | Heyn et al. . |
| 5,221,261 | 6/1993 | Termin et al. . |
| 5,234,456 | 8/1993 | Silvestrini . |
| 5,234,457 | 8/1993 | Andersen . |
| 5,266,073 | 11/1993 | Wall . |
| 5,282,823 | 2/1994 | Schwartz et al. . |
| 5,314,444 | 5/1994 | Gianturco . |
| 5,314,472 | 5/1994 | Fontaine . |
| 5,330,500 | 7/1994 | Song . |
| 5,342,300 | 8/1994 | Stefanadis et al. . |
| 5,344,425 | 9/1994 | Sawyer . |
| 5,378,239 | 1/1995 | Termin et al. . |

FOREIGN PATENT DOCUMENTS

| | | |
|---|---|---|
| 421729 | 4/1991 | European Pat. Off. . |
| 0 547 739 | 8/1992 | European Pat. Off. . |
| 565251 | 10/1993 | European Pat. Off. . |
| WO 92/13483 | 8/1992 | WIPO . |
| WO 93/19803 | 10/1993 | WIPO . |
| WO 94/16629 | 8/1994 | WIPO . |
| WO 94/16646 | 8/1994 | WIPO . |

OTHER PUBLICATIONS

Article by B.D. Cullity, *Elements of X–Ray Diffraction*, Second Edition, date unknown.
Brochure of Latrobe Steel Company, *Nickel–cobalt base alloy of the Multiphase alloy system*, dated Aug. 1981.
FDA, *Guidance for the Submission of Research and Marketing Applications for Interventional Cardiology Devices: PTCA Catheters, AtherectomyCatheters, Lasers, Intravascular Stents*, dated May 1994.

*Primary Examiner*—John G. Weiss
*Assistant Examiner*—John M. Black
*Attorney, Agent, or Firm*—Watts, Hoffmann, Fisher & Heinke

[57] ABSTRACT

An endoprosthesis includes a body structure formed of a biocompatible material, the body structure including a first material having an average atomic number greater than 24 and a second material that is different than the first material. The first material is present in an amount not greater than 9% by volume based on the combined volume of the first material and the second material. The body structure has a mass absorption coefficient effective to provide a ratio of an intensity of an incident X-ray to an intensity of a transmitted X-ray in a range of $1e^{-2}$ to $1e^{-4}$.

42 Claims, 2 Drawing Sheets

5,733,326

COMPOSITE MATERIAL ENDOPROSTHESIS

TECHNICAL FIELD

The present invention relates to endoprostheses, and in particular, to endoprostheses made of composite materials having radiographic contrast suitable for detection by X-ray fluoroscopy with minimal interference in rendering Quantitative Coronary Angiographic Analysis.

BACKGROUND OF THE INVENTION

One type of endoprosthesis device, commonly referred to as a stent, is placed or implanted within a blood vessel for treating stenoses, strictures, or aneurysms in the blood vessel. These devices are implanted within the vascular system to reinforce diseased, partially occluded, weakened or abnormally dilated sections of the blood vessel. Stents also have been successfully implanted in the urinary tract or the bile ducts to reinforce and prevent neoplastic growth in blood vessels. One common procedure for implanting the stent is to wrap the stent around a balloon catheter, to place the stent in the diseased portion of the vessel, for example, and then to inflate the balloon to secure the stent in place in the vessel.

Stents must be manufacturable and have suitable physical properties including suitable radiopacity, biocompatibility, and mechanical properties such as hoop strength, fatigue resistance, and corrosion resistance. Many stents today are composed of stainless steel or other metals which in their product thickness are not easily detectable using X-ray fluoroscopy. Stents have been constructed from tantalum wire, as disclosed in U.S. Pat. No. 5,135,536. However, tantalum wire is very radiopaque and thus, produces a very bright X-ray fluoroscopy image, which obscures the resulting X-ray image resulting from the surrounding tissue and prevents the use of Quantitative Coronary Angiographic techniques for lumen size determination.

It is currently difficult to alter the radiopacity of an endoprosthesis without changing its physical properties. Physical properties of the endoprosthesis are very important. Some stents have very limited compliance characteristics, making them not particularly well suited for use in curved vessel pathways. For example, using stents having a generally rigid cylindrical shape in curved vessel pathways typically requires the stents to have a very short length and to be strung out along the curved pathway. Also, such stents are often delivered separately, thereby increasing the invasiveness of the procedure.

Previous approaches in endoprosthesis construction have used devices with good hoop strength. When stents are provided in relatively large vessels or deployed within a vessel susceptible to external forces, such as within the leg, good hoop strength is important to resist forces which tend to collapse the endoprosthesis.

Other endoprostheses exhibit less hoop strength but are more compliant and are better suited to conform to the contour of the vessel, rather than being so non-conforming as to misshape the vessel after deployment. A typical disadvantage of more compliant stent devices is that they tend to deform upon or after deployment and present stenting surfaces that can lack desirable uniformity throughout the working surface area of the stent. A non-uniform working surface area of the stent is especially evident during expansion of the stent from its collapsed, insertion diameter to its expanded, implanted diameter. At times, this lack of uniformity upon expansion is exacerbated by folds or other non-uniformities in the balloon on which the stent is mounted for deployment.

SUMMARY OF THE INVENTION

The present invention is directed to a composite material endoprosthesis with predetermined radiopacity characteristics that do not compromise the physical properties of the endoprosthesis.

In general, the invention relates to an endoprosthesis including a body structure formed of a biocompatible material. The body structure includes a first material having an average atomic number greater than 24 and a second material that is different than the first material. The first material is present in an amount not greater than 9% by volume based on the combined volume of the first material and the second material. The body structure has a mass absorption coefficient effective to provide a ratio of an intensity of an incident X-ray to an intensity of a transmitted X-ray in a range of $1e^{-2}$ to $1e^{-4}$. More specifically, either the endoprosthesis itself or a stent made from this material has a tensile strength of 80,000–140,000 pounds per square inch ("psi") with a minimum elongation of 10 percent.

In a preferred embodiment, the body structure includes an elongated central cylindrical core and an elongated outer tubular member disposed around the core. One of the first and second materials comprises the core and the other comprises the tubular member. It is preferred that the first material comprise the core and the second material comprise the tubular member. However, an endoprosthesis may be constructed to have a tubular member comprised of the first material with a core comprised of the second material.

Instead of having a tubular member and core, the body structure may include one or more generally planar layers, one of the first and second materials comprising one of the layers and the other comprising another of the layers. The body structure may also be in the form of a cylindrical tube comprising a central layer along with at least one sheath disposed around the central layer. The central layer is comprised of the first material and the sheath is comprised of the second material.

The first material preferably comprises one or more of gold, platinum, tantalum, iridium, tungsten, and alloys thereof. The second material may be a cobalt alloy such as an alloy including cobalt, carbon, manganese, silicon, phosphorus, sulfur, chromium, nickel, molybdenum, titanium and iron, or any combination thereof. Other materials may be used for the second material, such as an alloy including cobalt, carbon, manganese, silicon, chromium, nickel, phosphorus, molybenum, iron and sulfur.

Certain materials are not preferred for use in the endoprostheses of the present invention. For example, when present in excessive amounts, palladium, copper, zinc and lead are toxic in the human body and would require a protective coating to be usable. Magnetic or ferromagnetic materials are undesirable for use in the endoprostheses of the present invention when used in excessive amounts. When a patient has a stent made of a magnetic or ferromagnetic material in the body, the use of Magnetic Resonance Imaging ("MRI") could be a problem since the stent may cause an artifact of the MRI image, be displaced by the magnetic field or heat up in the magnetic field. This prevents stents made of magnetic and ferromagnetic materials from being used in the brain for which an MRI Spiral Computerized Tomography ("CT") procedure is commonly performed.

Selecting the size of the tubular member is important for achieving the desired radiographic contrast depending upon the particular application. The tubular member has an outer diameter ranging from 0.0020 to 0.0150 inches and, more preferably, an outer diameter ranging from 0.0040 to 0.0100 inches. Even more preferably, the outer diameter of the tubular member ranges from 0.0050 to 0.0075 inches. The core has a diameter ranging from 0.0005 to 0.0030 inches.

The present invention avoids the problems of conventional endoprostheses materials having fluoroscopic signatures that are either too dim such as observed with stainless steel endoprostheses, or are too bright as in the case of endoprostheses comprising only tantalum. The endoprostheses of the present invention obtain good radiographic contrast without adversely altering their necessary physical properties. The radiographic contrast is obtained by selecting the mass absorption coefficient to provide a ratio of an intensity of an incident X-ray to an intensity of a transmitted X-ray in a range of $1e^{-2}$ to $1e^{-4}$. Thus, the endoprostheses of the present invention are bright enough to be seen during X-ray fluoroscopy but dim enough to allow the surrounding vessel or tissue to be seen through the endoprostheses and to perform Quantitative Coronary Angiography techniques.

The endoprostheses of the present invention are suitable for any application in which tailored radiographic contrast and physical properties are desirable. The endoprostheses may be formed into different sizes and shapes, as well as with different physical properties, depending upon where they are used in the body. The endoprostheses may advantageously be used to form coronary stents, peripheral stents, stent grafts and the like. The endoprostheses of the invention may also be used to form suture clips, vena cava filters, heart valves, guidewires and tube stiffening systems such as Palmaz stents by Johnson & Johnson Interventional Systems.

Other embodiments of the invention are contemplated to provide particular features and structural variants of the basic elements. The specific embodiments referred to as well as possible variations and the various features and advantages of the invention will become better understood from the detailed description that follows, together in connection with the accompanying drawings.

DETAILED DESCRIPTION OF PREFERRED EMBODIMENTS

Figure 1:
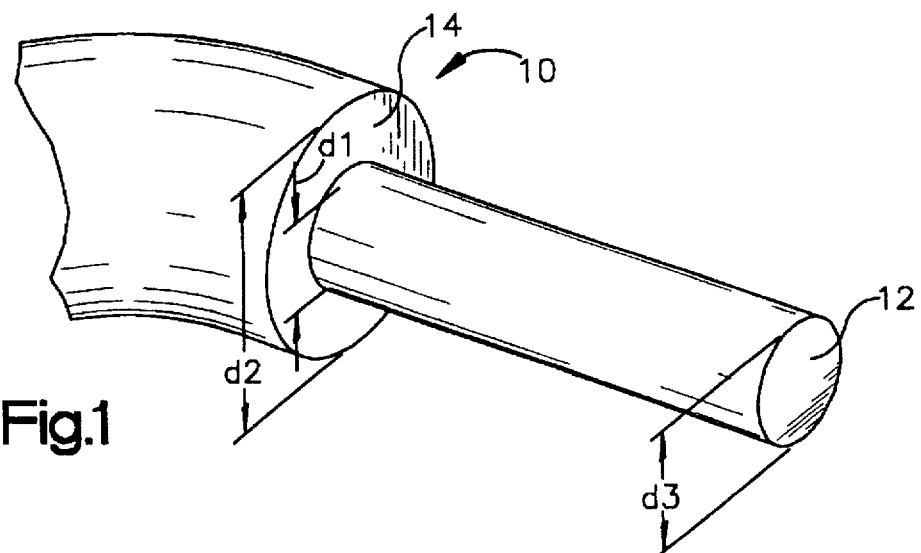
FIG. 1 is a perspective cross-sectional view showing one embodiment of an endoprosthesis constructed in accordance with the present invention.

Turning now to the drawings, FIG. 1 shows one form of an endoprosthesis 10 having a body structure including a biocompatible material. Each endoprosthesis 10 of the present invention has a composition that preferably includes two or more materials, a radiopaque first material and a second material that is different than the first material and imparts certain properties to the body structure.

The body structure is preferably in the form of an elongated wire member including a central cylindrical core 12 and an outer tubular sheath 14 disposed around the core 12. The core 12 and the sheath 14 both have a generally uniform transverse cross-sectional area along their lengths. The sheath 14 has an inner diameter d1 and an outer diameter d2. The inner diameter d1 of the sheath 14 is of a size sufficient to accommodate the core 12, which has a diameter d3. The body structure may have additional, generally annular layers disposed radially outside the sheath 14 or between the sheath 14 and the core 12. Alternatively, the body member may be formed from a single composite material as a solid cylindrical wire without a tubular sheath and a central cylindrical core.

Figure 2:
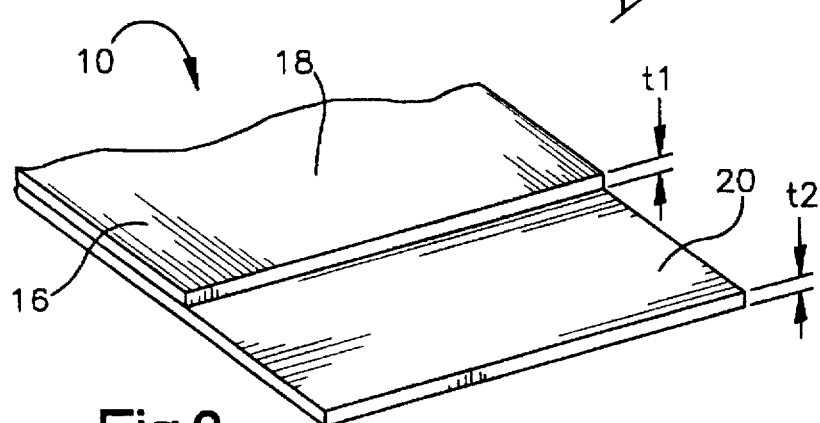
FIG. 2 is a perspective cross-sectional view showing another embodiment of an endoprosthesis constructed in accordance with the present invention.

FIG. 2 shows another form of the endoprosthesis 10 of the present invention, including a laminate structure 16 having first and second layers 18, 20. The first layer 18 has a thickness t1 and the second layer 20 has a thickness t2. Additional layers may also be used either between or outside the first and second layers 18, 20.

Figure 3:
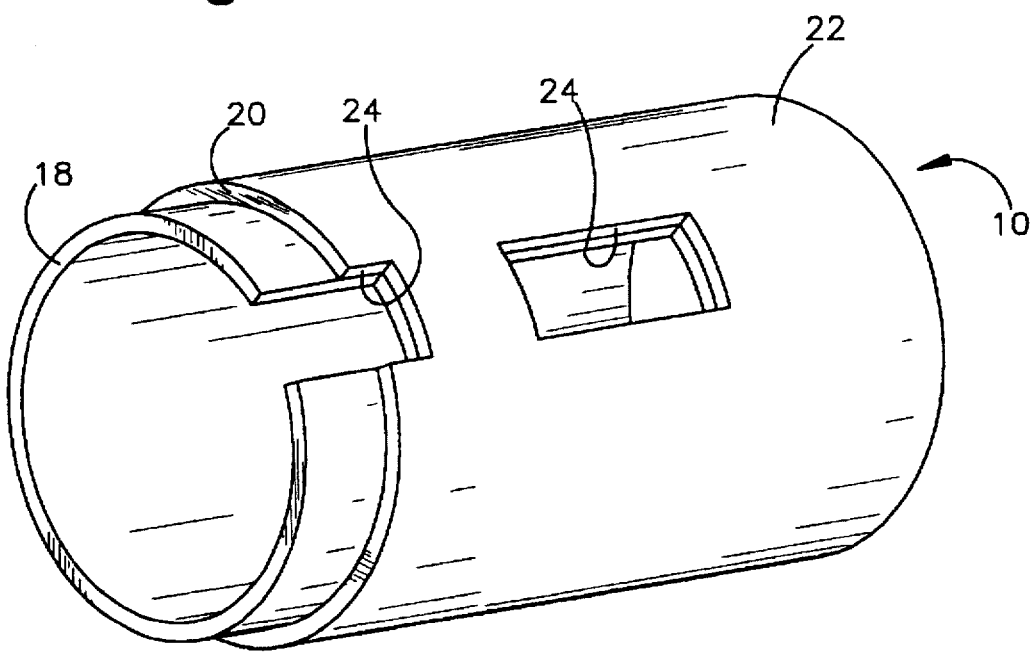
FIG. 3 is an endoprosthetic tube formed from the endoprosthesis shown in FIG. 2.

A cylindrical hypotube 22 shown in FIG. 3 may be formed from the laminate structure 16 of FIG. 2. In the hypotube configuration shown in FIG. 3, the layer 18 forms an inner tubular layer and the layer 20 forms an outer tubular layer.

Openings or windows 24 may be formed in the walls of the hypotube 22. The windows are preferably cut from the composite tube 22 to allow the endoprosthesis to be expandable to different diameters. The windows allow beam sections to develop between windows which will have elastic and plastic zones, which is consistent with the stent configuration by Palmaz developed by Johnson and Johnson Interventional Systems.

It is important to be able to detect the position of the endoprosthesis 10 using X-ray fluoroscopy or Magnetic Resonance Imaging during deployment and post deployment inspections of the endoprosthesis. The endoprosthesis 10 is detected when the material in the endoprosthesis body structure absorbs a sufficient intensity of a transmitted X-ray beam to be detected as a different intensity than the intensity of an initial X-ray beam. This relationship is empirically presented by the following equation:

$$I_x = I_0 e^{-(\mu/\rho)\rho x} \tag{1}$$

where:

$I_x$ is the intensity of the transmitted X-ray beam after passing through a thickness x;

$I_0$ is the intensity of the incident X-ray beam;

$\mu/\rho$ is the mass absorption coefficient of the endoprosthesis;

$\mu$ is the linear absorption coefficient;

$\rho$ is the density of the endoprosthesis; and x is the thickness or diameter of the endoprosthesis.

Equation 1 may be used for determining the radiopacity of each element and each alloy in the core, the sheath and the layers of the composite endoprosthesis structure.

The mass absorption coefficient of the composite endoprosthesis 10 used in Equation 1 is determined by summing the weight fractions of the mass absorption coefficients of each elemental component of the complete endoprosthesis. The mass absorption coefficient of each elemental component is related to the X-ray wavelength of the incident X-ray and the atomic number of each elemental component as follows:

$$\mu/\rho = k\lambda^3 Z^3 \tag{2}$$

where:

µ/ρ is the mass absorption coefficient of each elemental component;

k is a constant;

λ is the X-ray wavelength; and

Z is the atomic number of each elemental component.

By summing the elemental weight fraction multiplied by the elemental atomic number and the X-ray fluoroscope X-ray wavelength, for each element in the composite endoprosthesis, the mass absorption coefficient of the entire composite endoprosthesis can be determined.

Radiographic contrast is the difference in X-ray intensity transmitted through one interaction area of a material as compared to that transmitted through another interaction area of the material. Radiographic contrast is the relationship between the transmitted X-ray beam through the endoprosthesis and the transmitted X-ray beam through the surrounding tissue. Radiographic contrast for an endoprosthesis is defined as follows:

$$I_s/I_t \qquad (3)$$

where:

$I_s$ is the intensity of the X-ray beam transmitted through the endoprosthesis; and $I_t$ is the intensity of the X-ray beam through tissue.

The X-ray intensity of the composite endoprosthesis 10 and the surrounding tissue used in Equation 3 can be calculated using Equation 1. The radiographic contrast between tissue and bone is approximately equal to one.

The present invention permits the radiographic contrast of the endoprosthesis to be predetermined by controlling the mass absorption coefficient. The mass absorption coefficient is controlled by selecting the composite material used and the thickness or diameter of the entire endoprosthesis, ie., d2 or t1+t2. By using preferably two or more materials, each having different physical properties, the radiographic contrast may be adjusted as desired without altering the physical properties of the entire endoprosthesis including fatigue resistance, corrosion resistance, tensile strength, toughness and biocompatibility. This is because by employing a structure having a tubular member and core, for example, the amount of the radiopaque material in the core can be adjusted while maintaining the amount of the structural material in the tubular member needed for the requisite physical properties.

The mass absorption coefficients must be carefully selected to produce a radiographic contrast within a preferred range. It is important to design the composite structure so that the fluoroscopy signature of the endoprosthesis is adequately detectable or bright, and yet does not develop an X-ray artifact which interferes with X-ray signatures of the vessel wall. In other words, the X-ray fluoroscopy images of the radiopaque materials must not be excessively bright. Experimental studies on the radiopacity of endoprostheses of the present invention using adult mongrel canine and pygmy swine porcine have indicated that the ideal fluoroscopic signature correlates to a radiographic contrast in a range of $1e^{-2}$ to $1e^{-4}$. This contrast range provides sufficient intensity to detect the endoprosthesis without, for example, altering quantitative angiographic measurement.

Figure 4:
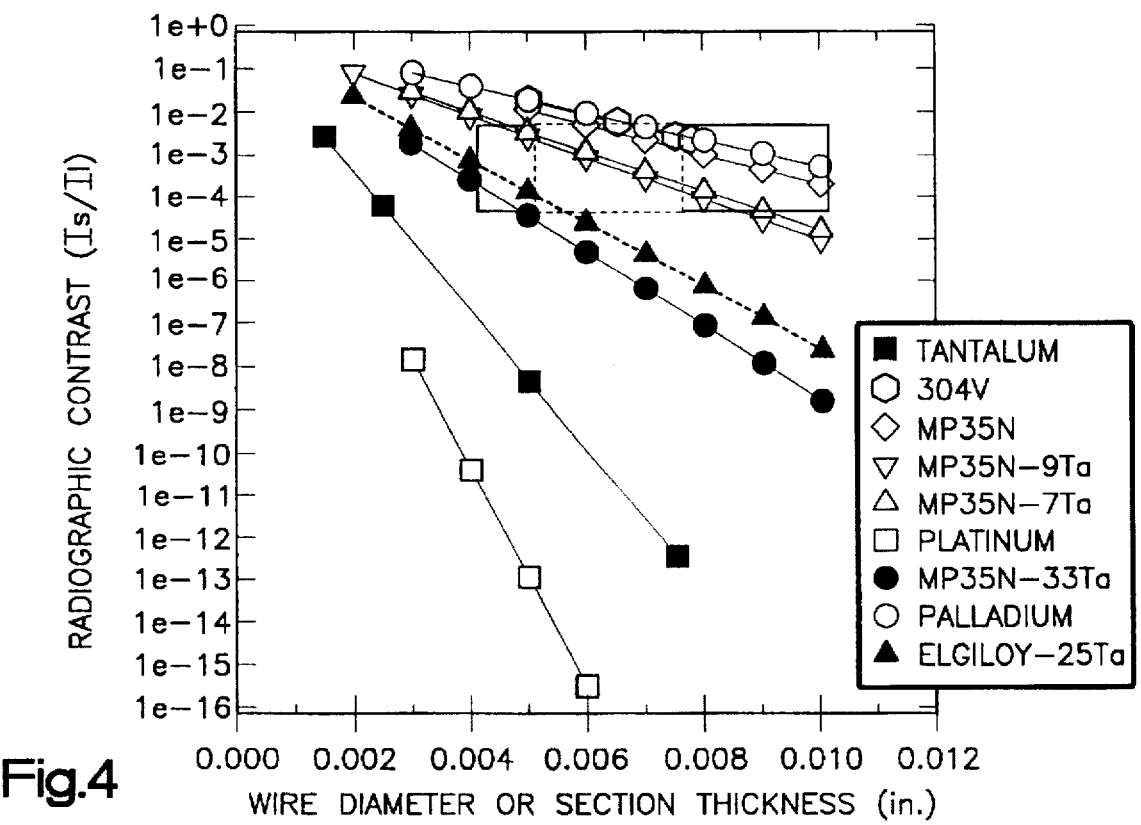
FIG. 4 is a graph showing radiographic contrast as a function of wire diameter or section thickness.

FIG. 4 shows the radiographic contrast versus outer diameter d2 in the FIG. 1 configuration or sector thickness (t1+t2) in the FIG. 3 configuration for different material systems. The rectangular region defined by the solid lines along the x-axis between 0.0040 and 0.0100 inches is a region of desired radiographic contrast. This region of desired radiographic contrast corresponds to ideal fluoroscopic conditions for stents composed of laminate layers in a tube configuration and for large diameter wire used in large diameter vessels such as an aortic or vena cava lumen.

The rectangular region defined by the dotted lines along the x-axis in FIG. 4 between 0.0050 and 0.0075 inches is a region of preferred radiographic contrast. This preferred region corresponds to ideal fluoroscopic conditions for coronary and peripheral stents composed of wire. The following description herein, unless otherwise indicated, refers to the wire embodiment shown in FIG. 1, although it is equally applicable to the laminate and hypotube embodiments shown in FIGS. 2 and 3.

Both the desirable and preferred radiographic contrast regions fall within the predetermined requisite radiographic contrast range along the y-axis of $1e^{-2}$ to $1e^{-4}$. The radiographic contrast range of the present invention is particularly important in the case of stents which, when expanded, enter the vessel wall. After the resultant restenosis it is important to be able to see the vessel wall through the stent. For this reason, the endoprosthesis needs to be bright enough during X-ray fluoroscopy to be seen, but dim enough to be seen through. Being able to see through the endoprosthesis means that the X-ray signature from the endoprosthesis does not create an X-ray artifact which masks the surrounding vessel and tissue. This allows an accurate measurement of the vessel lumen size after implantation. At radioscopic contrast greater than $1e^{-2}$ the endoprosthesis is too dim for the endoprosthesis to be seen. X-ray images showing the radiographic contrast of $1e^{-2}$ were observed in a canine study of the endoprostheses of the present invention at the Institut de Cardiologie de Montreal and were presented on a real time video and on X-ray film. At radiographic contrast less than $1e^{-4}$ the endoprosthesis is too bright for the surrounding tissue or vessel wall to be seen. Thus, the endoprostheses of the present invention are constructed to have a range of radiographic contrast between $1e^{-2}$ to $1e^{-4}$, which strikes a balance between seeing the endoprosthesis and seeing the surrounding vessel wall or tissue during X-ray fluoroscopy.

The sheath or outer tube 14 preferably has an outer diameter d2 ranging from 0.0020 to 0.0150 inches. More preferably, the sheath 14 has an outer diameter d2 ranging from 0.0040 to 0.0100 inches, as shown by the combined range of the desirable and preferred radiographic contrast regions in FIG. 4. Even more preferably, the sheath 14 has an outer diameter d2 ranging from 0.0050 to 0.0075 inches, as shown by the preferred dotted region in FIG. 4. A core diameter d3 ranging from 0.0010 to 0.0025 inches achieves optimal radiographic contrast for all applications.

The core and sheath diameters d1, d2 and d3 of the composite endoprosthesis 10 vary depending upon the intended use of the endoprosthesis 10. When the endoprostheses 10 are used to form coronary stents, the outer diameter d2 ranges from 0.0050 to 0.0060 inches. For use in saphenous vein grafts the outer diameter d2 ranges from 0.0055 to 0.0065 inches. For peripheral stents, such as for use in iliac and biliary lumens, for use in the brain, and for abdominal aortic aneurysms, the outer diameter d2 ranges from 0.0075 to 0.0100 inches. The laminate structure 16 has an overall size (t1 and t2) that varies depending upon the application of the endoprosthesis and may have the same sizes as the outer wire diameter d2 and the core diameter d3 discussed above.

Figure 5:
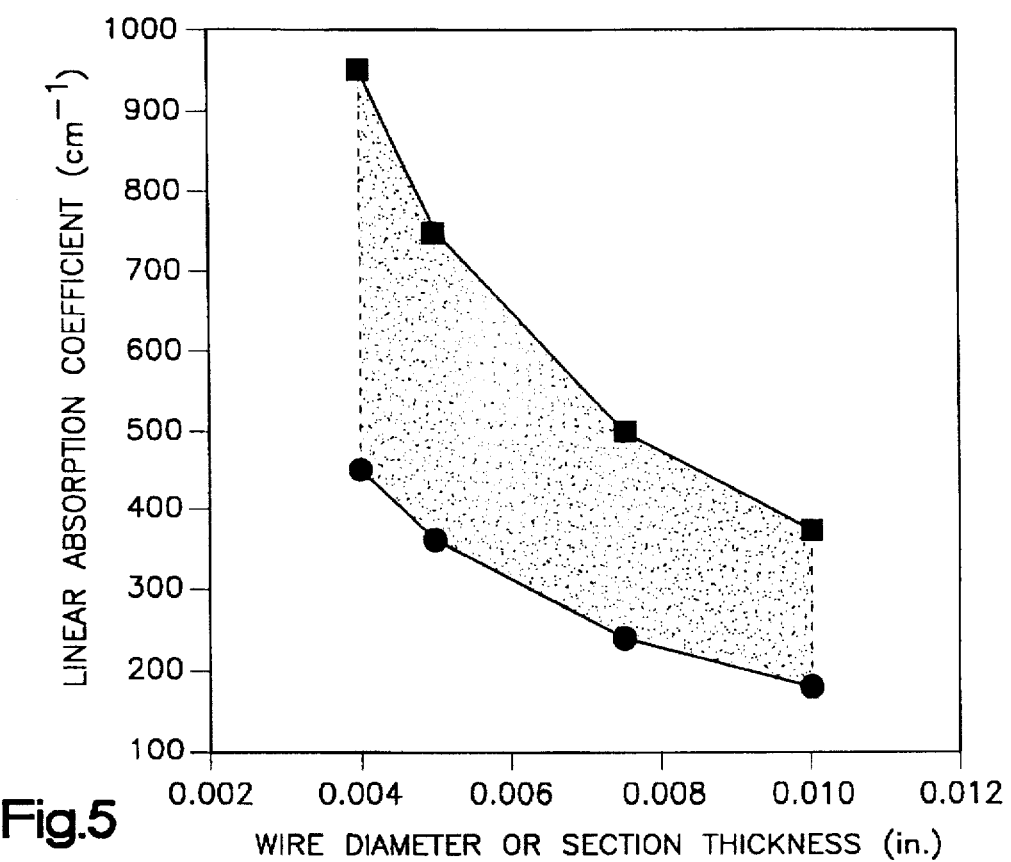
FIG. 5 is a graph showing linear absorption coefficient as a function of wire diameter or section thickness.

FIG. 5 shows linear absorption coefficient as a function of wire diameter or section thickness. The shaded region shows the desired linear absorption coefficient across outer wire diameters d2 ranging from 0.0040 to 0.0075 inches.

The following Table I shows average atomic numbers, and hence elements that may be used, to form a composite endoprosthesis with radiographic contrast ranging from $1e^{-2}$ to $1e^{-4}$.

TABLE I

| Wire Diameter or Section Thickness (inch) | Average atomic number |
| --- | --- |
| 0.004 | 63–71 |
| 0.0050 | 28–70 |
| 0.0075 | 26–64 |
| 0.0100 | 24–27 |

A unique and important characteristic of the present invention is its ability to use multiple materials that each exhibit superior performance for some of the required physical properties. The core is preferably selected to provide the composite endoprosthesis with good radiopacity while the sheath is preferably selected to provide the composite endoprosthesis with good physical properties. An endoprosthesis may thus be designed to have suitable radiographic contrast without adversely affecting the physical properties of the endoprosthesis.

The first material includes one or more materials with an atomic number (elemental) or an average atomic number ranging from 24–71, as shown in Table I. For example, the first material preferably includes one or more of gold, platinum, tantalum, iridium, tungsten, and alloys thereof. A preferred first material, tantalum, may be obtained from the Cabot Corporation.

The second material has chemical and physical properties that are compatible with the first material. The second material may be a nickel cobalt alloy such as an alloy including cobalt, carbon, manganese, silicon, phosphorus, sulfur, chromium, nickel, molybdenum, iron and titanium, or any combination thereof. Other materials may be used for the second material, such as an alloy including cobalt, carbon, manganese, silicon, chromium, nickel, phosphorus, molybdenum, sulfur and iron.

One composition for the second material is known as 304V supplied by Carpenter Technology Corporation and has the following nominal composition (% by weight): carbon: 0.03 maximum; manganese: 2.00 maximum; silicon: 1.00 maximum; chromium: 18.0–20.0; nickel: 8.0–12.0; phosphorus: 0.045 maximum; sulphur: 0.03 maximum; with the balance being iron.

Another composition for the second material is known as 316 LVM supplied by Carpenter Technology Corporation and includes the following nominal composition (% by weight): carbon: 0.03 maximum; manganese: 2.00 maximum; silicon: 1.00 maximum; chromium: 16.0–18.0; nickel: 10.0–14.0%; phosphorus: 0.045% maximum; sulfur: 0.03% maximum; molybdenum: 2.0–3.0; with the balance being iron.

A preferred composition for the second material is known as MP35N (supplied by Carpenter Technology Corporation and the Latrobe Steel Company) and has the following nominal composition (% by weight): carbon: 0.025 maximum; manganese: 0.15 maximum; silicon: 0.15 maximum; phosphorus: 0.015 maximum; sulfur: 0.010 maximum; chromium: 19.0–21.0 maximum; nickel: 33.0–37.0; molybdenum: 9.0–10.5; iron: 1.0 maximum; titanium: 1.0 maximum; with the balance being cobalt.

In the composite body structure of the present invention the first material is present in an amount of 2–9% by volume based on the combined volume of the first and second materials. One preferred composite material includes 91 volume % MP35N and 9 volume % Ta. Other preferred composite materials include either 93 volume % MP35N and 7 volume % Ta or 96 volume % MP35N and 4 volume % Ta. These materials exhibit radiographic contrasts that fall completely within the preferred dotted region across wire diameters in the range of from 0.0050 to 0.0075 inches.

Other endoprosthesis materials are those that comprise only tantalum or platinum and a material including 67 volume % MP35N and 33 volume % Ta (MP35N-33Ta). These materials have X-ray fluoroscopic signatures that are generally too bright for the surrounding tissue or vessel wall to be seen.

Although the lower limit of the desirable region of wire diameter is shown as 0.0040 inches in FIG. 4, a wire diameter of 0.0050 inches or more is preferable. At wire diameters under 0.0050 inches, the endoprosthesis does not possess desirable hoop strength. A minimum hoop strength of 100 mm of Hg must be maintained for an endoprosthesis. An endoprosthesis having the configuration shown in FIG. 1 should have a 0.0040 inch diameter or greater to satisfy this hoop strength. An endoprosthesis having the configuration shown in FIG. 3 may require a thickness of 0.0030 or 0.0020 inches to satisfy this hoop strength. Therefore, although the MP35N-33Ta composition and other materials with a high radiopaque material content may have acceptable radiographic contrast under 0.0050 inches in wire diameter as shown in FIG. 4, it may not be feasible to make endoprostheses from such materials, due to their undesirably low hoop strengths.

Although an endoprosthesis composed of a single material system such as one of palladium, MP35N or 304V falls within the region of acceptable radiographic contrast as shown in FIG. 4, these materials have certain drawbacks. Palladium is toxic in the human body and would require a protective coating to be usable. An endoprosthesis comprising either MP35N or 304V alone only has acceptable contrast for wire diameters in excess of about 0.0060 inches, which prevents these materials from being used for coronary stents.

Iron-based materials are undesirable in the endoprosthesis of the present invention when present in excessive amounts. One such iron-based material that is undesirable for use in the present invention has the brand name of Elgiloy, and may be obtained from the Carpenter Technology Corporation. Such iron-containing stents in the body undesirably heat up and move when an MRI Spiral CT is performed on the patient.

The endoprostheses of the present invention are made by obtaining composite filaments manufactured by a drawn filled tubing ("DFT") process such as that performed by Ft. Wayne Metals Research Products Corporation of Ft. Wayne, Ind. A tube made of the second material has an inner diameter that permits a core wire made of the first material to be inserted into it and to be substantially radially centered in the tube. The inner and outer diameters of the tube and the diameter of the core wire vary depending on the materials used. The inside and outside diameter of the sheath material and the outside diameter of the core material at the start of the manufacturing process vary based upon the particular starting material and the desired percent by volume of the core. The tube and core wire may be at least twenty feet in length. The core wire is inserted into a central opening of the tube to form a composite filament.

The filament then undergoes a plurality of alternating cold working and annealing steps. For example, the filament may be drawn through three dies. In each die, the filament is cold worked in radial compression, which causes it to flow, thereby reducing its diameter and increasing its length. The tube may be radially reduced and lengthened more rapidly than the wire at first, due to a gap initially present between the wire and the tube. After the gap is closed, the core wire and tube are radially reduced and lengthened at substantially the same rate.

Passing through each of the dies induces strain hardening and other stresses into the filament, which are removed by one or more annealing steps. In each of the annealing steps the filaments are heated at a temperature ranging from about 1900° to about 2300° F. Each annealing step removes nearly all of the induced stresses from the filament. Each annealing step may last between, for example, 1 to 30 seconds at the annealing temperature, depending on the size of the filament. The number of cold working and annealing steps depends on the initial filament size, the materials used and the desired radial reduction. In the wire drawing process, the composite material is drawn down in successive dies at a 10% reduction in area per die. Between each annealing cycle there is a 30 to 50% reduction in area.

The resulting endoprosthesis may then be formed into a stent by a process known to those skilled in the art, such as that described in U.S. patent application Ser. No. 08/123,440 to Williams, entitled "Endoprosthesis Having Laser Welded Junctions, Method and Procedure," filed Jun. 16, 1995, which is incorporated herein by reference in its entirety.

The laminate hypotube may be manufactured by one of two processes. In the first process the hypotube may be produced by hot rolling a series of layers of material into a laminate sheet. Each layer includes one or more layers of the second structural material such as MP35N and one or more layers of the first radiopaque material such as tantalum. The hot rolling process may be optimized to ensure mechanical bonding between the multiple layers and that the composite material has a tensile strength ranging from 70,000 to 120,000 psi with 5 to 30 percent elongation. Elongation is defined as the percent increase in the length of a component prior to failure when a tensile load is applied to the component. The laminate sheets may then be rolled up around a mandrel and seam welded to form a tube. The seam welded tube can then be drawn to final size.

The second process for making the hypotube is to place multiple layers of tubes within each other around a core mandrel. The composite structure may then be drawn and heat treated using conventional wire drawing practices until the finished tube diameter meets the physical properties and dimensions required. A sacrificial ductile core mandrel is placed within the hypotube prior to the wire drawing process. The composite system is then drawn to finish dimensions and the core mandrel is removed. Removal of the mandrel is achieved by reducing the cross section of the mandrel. By solely pulling the mandrel, the diameter of the mandrel can be reduced sufficiently to be easily removed.

Once a composite hypotube is obtained, the structure may be loaded onto a lathe type tool and windows may be cut from this tube using, for example, a laser, a cutting tool, a water saw, or an electron discharge machining ("EDM") process. In the EDM process a wire is used as a cutting tool and placed in contact with the part. An electrical pulse is transferred through the wire and an electrical discharge occurs, burning a fine cut in the part. The EDM process accurately cuts the part without inducing stresses in it. Once the windows are cut from the tube, the tube may then be deburred by a procedure such as shot peening, abrasive tumbling, honing, electropolishing and electroetching.

The windows are important to the function of the endoprosthesis. When the endoprosthesis is in the form of a stent, the stent is required to be crimped down onto a balloon catheter at a size smaller than the original hypotube and deployed to a size at less than twice the diameter of the hypotube. To achieve this task, regions need to exist within the endoprosthesis where plastic deformation can result in thin sections allowing the expansion and contraction of the endoprosthesis to occur at a low pressure of approximately 2 atmospheres.

The core and sheath materials are preferably selected to have physical properties, such as coefficients of thermal expansion, annealing temperature ranges, and elastic moduli, which are compatible with each other. Matching the Young's Moduli of the core and sheath materials is well within the ability of those skilled in the art in view of the instant disclosure, and is an important part of developing the material of the present invention. The component with the largest cross-sectional area must have a Young's Modulus equal or greater to the Young's Modulus of the other component. If this does not occur, the multiple layers of the endoprosthesis will delaminate during the manufacturing process or during in vivo use. The endoprosthesis material must also be biocompatible and not toxic so that it will not result in an inflammatory reaction from the body.

Important mechanical properties for the endoprostheses of the present invention are toughness, tensile strength and hoop strength. The composite structure or alloy must have sufficient toughness, i.e., enough resistance to failure to prevent the initiation and propagation of cracks during the stress history of the endoprosthesis. The stress history includes the application of a load during the manufacturing process and during deployment, and cyclic loading in the human body. The endoprothesis may have a toughness ranging from 20 to 120 joules.

It is preferred that the endoprosthesis, or a stent, for example, that is made from the endoprosthesis, be plastically deployed by a balloon. Such an endoprosthesis or a stent made therefrom has an ultimate tensile strength in the range of 80,000–140,000 psi and 10% minimum elongation and, more preferably, an ultimate tensile strength of 80,000 to 110,000 psi. A minimum hoop strength of 100 mm of Hg is required to keep a vessel open.

The surface of the sheath or outer laminates is preferably free of imperfections with a surface finish of no more than 30 μin roughness. Such a surface finish minimizes the development of crack nucleation sites on the surface of the endoprosthesis. A defect-free surface minimizes the incidence of fatigue failure as well as the possibility of thrombus generation and tissue inflammation.

The composite material must also be corrosion resistant as specified in the document, *Guidance for the Submission of Research and Marketing Applications For Interventional Cardiology Devices: PTCA Catheters Atherectomy Catheters Lasers Intervascular Stents*, the Interventional Cardiology Branch Division of Cardiovascular, Respiratory and Neurological devices Office of Device Evaluation, May 1994. In a ten year product life in saline, the composite structure is preferably sufficiently noble to prevent surface corrosion from degrading the endoprothesis, and must prevent crevice corrosion or galvanic corrosion from degrading the endoprothesis between the layers.

Although the invention has been described in its preferred form with a certain degree of particularity, it will be understood that the present disclosure of the preferred embodiments has been made only by way of example and that various changes may be resorted to without departing from the true spirit and scope of the invention as hereafter claimed.

What is claimed is:

1. An endoprosthesis including a body structure formed of a biocompatible material, said body structure including a first material having an average atomic number greater than 24 and a second material that is different than said first material, said first material being present in an amount not greater than 9% by volume based on a combined volume of said first material and said second material, wherein said body structure has a mass absorption coefficient effective to provide a ratio of an intensity of an incident X-ray to an intensity of a transmitted X-ray in a range of $1e^{-2}$ to $1e^{-4}$ and wherein the endoprosthesis has a tensile strength ranging from 80,000–140,000 pounds per square inch.

2. The endoprosthesis of claim 1 the endoprosthesis having a hoop strength of at least 6 pounds per square inch.

3. The endoprosthesis of claim 1 wherein said body structure comprises an elongated central cylindrical core and an elongated outer tubular member disposed around the core, one of said first and second materials comprising the core and the other of said first and second materials comprising the tubular member.

4. The endoprosthesis of claim 1 wherein said body structure comprises at least one layer, a first layer of said body structure being comprised of said first material and a second layer of said body structure being comprised of said second material.

5. The endoprosthesis of claim 3 said first material comprising the core and said second material comprising the tubular member.

6. The endoprosthesis of claim 1 said first material being selected from the group consisting of gold, platinum, tantalum, iridium, tungsten, and alloys thereof, and any combination thereof.

7. The endoprosthesis of claim 1 said second material comprising a nonmagnetic material.

8. The endoprosthesis of claim 1 said second material comprising carbon, manganese, silicon, chromium, nickel, phosphorus, sulfur and iron.

9. The endoprosthesis of claim 1 said second material comprising a cobalt alloy.

10. The endoprosthesis of claim 9 said second material being selected from the group consisting of carbon, manganese, silicon, phosphorus, sulfur, chromium, nickel, molybdenum, iron, titanium, and cobalt, and any combination thereof.

11. The endoprosthesis of claim 5 the tubular member having an outer diameter ranging from 0.0020 to 0.0150 inches.

12. The endoprosthesis of claim 5 the tubular member having an outer diameter ranging from 0.0040 to 0.0100 inches.

13. The endoprosthesis of claim 5 the tubular member having an outer diameter ranging from 0.0050 to 0.0075 inches.

14. The endoprosthesis of claim 5 the core having a diameter ranging from 0.0005 to 0.0030 inches.

15. An endoprosthesis including a body structure formed of a biocompatible material, said body structure being in the form of a wire comprising a central cylindrical core and an outer sheath disposed around said core, said core including a first material having an average atomic number greater than 24 and said sheath including a second material that is different than said first material, said first material being present in an amount not greater than 9% by volume based on a combined volume of said first material and said second material, and wherein said body structure has a mass absorption coefficient effective to provide a ratio of an intensity of an incident X-ray to an intensity of a transmitted X-ray in a range of $1e^{-2}$ to $1e^{-4}$ and wherein the endoprosthesis has a tensile strength ranging from 80,000 to 140,000 pounds per square inch.

16. The endoprosthesis of claim 15 said first material being selected from the group consisting of gold, platinum, tantalum, iridium, tungsten, and alloys thereof, and any combination thereof.

17. The endoprosthesis of claim 15 said second material comprising a cobalt alloy.

18. The endoprosthesis of claim 15 the tubular member having an outer diameter ranging from 0.0020 to 0.0150 inches.

19. The endoprosthesis of claim 15 the tubular member having an outer diameter ranging from 0.0040 to 0.0100 inches.

20. The endoprosthesis of claim 15 the tubular member having an outer diameter ranging from 0.0050 to 0.0075 inches.

21. The endoprosthesis of claim 15 the core having an outer diameter ranging from 0.0005 to 0.0030 inches.

22. The endoprosthesis of claim 15 the endoprosthesis having a hoop strength of at least about 6 pounds per square inch.

23. An endoprosthesis including a body structure formed of a biocompatible material, said body structure including a first material having an average atomic number greater than 24 and a second material that is different than said first material, said first material being present in an amount not greater than 7% by volume based on a combined volume of said first material and said second material, and wherein said body structure has a mass absorption coefficient effective to provide a ratio of an intensity of an incident X-ray to an intensity of a transmitted X-ray in a range of $1e^{-2}$ to $1e^{-4}$.

24. The endoprosthesis of claim 23 said body structure comprising an elongated central cylindrical core and an elongated outer tubular member disposed around the core, one of said first and second materials comprising the core and the other of said first and second materials comprising the tubular member.

25. The endoprosthesis of claim 23 said body structure comprising at least one layer, one of said first and second materials comprising one said layer and the other of said first and second materials comprising another said layer.

26. The endoprosthesis of claim 24 said first material comprising the core and said second material comprising the tubular member.

27. The endoprosthesis of claim 23 said second material being selected from the group consisting of carbon, manganese, silicon, phosphorus, sulfur, chromium, nickel, molybdenum, iron, titanium, and cobalt, and any combination thereof.

28. The endoprosthesis of claim 23 the endoprosthesis having a tensile strength ranging from 80,000–140,000 pounds per square inch.

29. The endoprosthesis of claim 23 said first material being selected from the group consisting of gold, platinum, tantalum, iridium, tungsten, and alloys thereof, and any combination thereof.

30. An endoprosthesis including a body structure formed of a biocompatible material, said body structure including a first material having an average atomic number greater than 24 and a second material that is different than said first material and nonmagnetic, said first material being present in an amount not greater than 9% by volume based on a combined volume of said first material and said second material, and wherein said body structure has a mass absorption coefficient effective to provide a ratio of an intensity of an incident X-ray to an intensity of a transmitted X-ray in a range of $1e^{-2}$ to $1e^{-4}$.

31. The endoprosthesis of claim 30 said body structure comprising an elongated central cylindrical core and an elongated outer tubular member disposed around the core, one of said first and second materials comprising the core and the other of said first and second materials comprising the tubular member.

32. The endoprosthesis of claim 30 said body structure comprising at least one layer, one of said first and second materials comprising one said layer and the other of said first and second materials comprising another said layer.

33. The endoprosthesis of claim 31 said first material comprising the core and said second material comprising the tubular member.

34. The endoprosthesis of claim 30 said second material being selected from the group consisting of carbon, manganese, silicon, phosphorus, sulfur, chromium, nickel, molybdenum, iron, titanium, and cobalt, and any combination thereof.

35. The endoprosthesis of claim 30 the endoprosthesis having a tensile strength ranging from 80,000–140,000 pounds per square inch.

36. The endoprosthesis of claim 30 said first material being selected from the group consisting of gold, platinum, tantalum, iridium, tungsten, and alloys thereof, and any combination thereof.

37. The endoprosthesis of claim 15 said second material being selected from the group consisting of carbon, manganese, silicon, phosphorus, sulfur, chromium, nickel, molybdenum, iron, titanium, and cobalt, and any combination thereof.

38. The endoprosthesis of claim 4 wherein the endoprosthesis is configured and arranged as a tube having a wall comprising said first layer and said second layer, each layer of said body structure having a generally annular shape.

39. The endoprosthesis of claim 38 wherein a wall thickness of said tube ranges from 0.0020 to 0.0150 inches.

40. The endoprosthesis of claim 38 wherein a wall thickness of said tube ranges from 0.0040 to 0.0100 inches.

41. The endoprosthesis of claim 38 wherein a wall thickness of said tube ranges from 0.0050 to 0.0075 inches.

42. The endoprosthesis of claim 38 wherein said first layer has a thickness ranging from 0.0005 to 0.0030 inches.

* * * * *